(12) United States Patent
Popescu

(10) Patent No.: US 8,841,910 B2
(45) Date of Patent: Sep. 23, 2014

(54) MAGNETIC RESONANCE DEVICE INCLUDING AN ANTENNA ARRANGEMENT

(75) Inventor: Stefan Popescu, Erlangen (DE)

(73) Assignee: Siemens Aktiengesellschaft, Münich (DE)

( * ) Notice: Subject to any disclaimer, the term of this patent is extended or adjusted under 35 U.S.C. 154(b) by 357 days.

(21) Appl. No.: 13/284,658

(22) Filed: Oct. 28, 2011

(65) Prior Publication Data

US 2012/0280687 A1 Nov. 8, 2012

(30) Foreign Application Priority Data

Oct. 29, 2010 (DE) .......................... 10 2010 043 134

(51) Int. Cl.
| | | |
|---|---|---|
| *G01V 3/00* | (2006.01) | |
| *G01R 33/3415* | (2006.01) | |
| *A61B 5/055* | (2006.01) | |
| *G01R 33/422* | (2006.01) | |
| *G01R 33/36* | (2006.01) | |

(52) U.S. Cl.
CPC ............ *G01R 33/3415* (2013.01); *A61B 5/055* (2013.01); *G01R 33/365* (2013.01); *G01R 33/422* (2013.01)
USPC ......................................................... 324/318

(58) Field of Classification Search
CPC ............. G01R 33/34; G01R 33/34046; G01R 33/34076; G01R 33/3415; G01R 33/38; G01R 33/385
USPC ................................................ 324/300–322
See application file for complete search history.

(56) References Cited

U.S. PATENT DOCUMENTS

| | | | |
|---|---|---|---|
| 6,771,070 B2 * | 8/2004 | Lee ................................ 324/318 |
| 7,088,104 B2 * | 8/2006 | Bottomley ..................... 324/328 |
| 7,501,823 B2 * | 3/2009 | Nistler et al. .................. 324/318 |
| 8,022,705 B2 * | 9/2011 | Bogdanov ..................... 324/318 |

FOREIGN PATENT DOCUMENTS

| | | |
|---|---|---|
| DE | 3410215 A1 | 10/1985 |
| DE | 199 14 989 A1 | 10/2000 |
| WO | WO 2007/104607 A1 | 9/2007 |

OTHER PUBLICATIONS

German Office Action dated Jul. 7, 2011 for corresponding German Patent Application No. DE 10 2010 043 134.6 with English translation.

* cited by examiner

*Primary Examiner* — Dixomara Vargas
(74) *Attorney, Agent, or Firm* — Lempia Summerfield Katz LLC

(57) ABSTRACT

A magnetic resonance device includes a measuring chamber, a high-frequency shield at least partially enclosing the measuring chamber and an antenna arrangement that includes a plurality of antenna elements disposed around the measuring chamber. The antenna elements have at least one component that is active in the manner of an antenna and extends, as viewed from the high-frequency shield, towards an interior of the measuring chamber.

20 Claims, 5 Drawing Sheets

US 8,841,910 B2

MAGNETIC RESONANCE DEVICE INCLUDING AN ANTENNA ARRANGEMENT

This application claims the benefit of DE 10 2010 043 134.6, filed on Oct. 29, 2010.

BACKGROUND

The present embodiments relate to a magnetic resonance device having a measuring chamber, a high-frequency shield at least partially enclosing the measuring chamber and an antenna arrangement installed in the magnetic resonance device.

In a magnetic resonance device, a body to be examined may be exposed with the aid of a basic field magnet system to a relatively high basic magnet field of 3 or 7 Tesla, for example. A magnetic field gradient is also applied with the aid of a gradient system. High-frequency excitation signals (HF signals) are emitted using suitable antenna facilities (e.g., suitable antenna devices) by way of a high-frequency transmit system. The nuclear spin in a specific region is tilted about a flip angle defined as an average compared with the magnetic field lines of the basic magnetic field due to this high-frequency field of resonantly excited atoms. This high-frequency excitation and the resulting flip angle distribution are also referred to as nuclear magnetization. As the nuclear spin relaxes, high-frequency signals (e.g., magnetic resonance signals) are emitted. The high-frequency signals are received by suitable receive antennas and are further processed. Raw data thus acquired may be used to reconstruct the desired image data. The high-frequency signals for nuclear spin magnetization may be transmitted by a body coil. The body coil may have the structure of a birdcage antenna that consists of a plurality of transmit rods disposed around the measuring chamber (e.g., the "patient chamber" or "patient tunnel"), parallel to the longitudinal axis of the tomography system. A patient is positioned in the measuring chamber during the examination. On end faces of the antenna rods, the antenna rods are connected capacitively to one another in a ring. The individual transmit rods may consist of conductor tracks equipped with defined reactances (e.g., capacitive elements). The ring segments connecting the transmit rods are in the form of conductor tracks with such reactances. Apart from the ring-type connections on the end faces, it is also possible (e.g., in the case of longer birdcage antennas) for the antenna rods also to be connected in the same manner in a ring shape at one or more points in a central region. The antenna elements of the body coil are disposed directly on a cylindrical tube made of plastic or the like. The cylindrical tube delimits the patient chamber. The antenna elements are attached, in the form of conductor tracks, directly to the tube or to conductor track films covering the tube. The tube may also be referred to as a support tube. The entire arrangement (e.g., the measuring chamber with the antenna arrangement) is enclosed by a high-frequency shield or high-frequency screen that screens the sensitive receive antennas from external interference signals.

The body coil may be used not only to transmit high-frequency pulses but also to receive magnetic resonance signals. Local coils may be used to receive magnetic resonance signals. The local coils are positioned directly on the body of the patient. The local coils may consist of a group or array of conductor loops. The antenna conductor loops may be operated individually. The antenna conductor loops are structured so that the antenna conductor loops may also detect the magnetic high-frequency field of a weak magnetic resonance signal with particular sensitivity. The signals induced in the antenna conductor loop may be amplified, and the amplified signal may be used as raw data after digitization.

Since the overall nuclear magnetization may rotate in the x/y plane (e.g., perpendicular to the longitudinal direction of the measuring chamber referred to as the z direction) in an excited region of the examination object, a magnetization vector for each rotation angle is also essentially perpendicular to the surface of the examination object or patient body. With such antenna conductor loops disposed in a tangential or parallel manner directly on the body surface, the maximum magnetic flux of the magnetic resonance signal is therefore captured. Thus, the maximum possible receive signal may also be induced in the antenna. Such an antenna array may form a relatively large surface antenna on the body of the examination object or patient. A further advantage of such an antenna array with a number of individually operable conductor loops is, for example, that in the context of parallel imaging methods, image acquisition is significantly accelerated, thereby reducing the temporal burden for the patient. Many patients find the positioning of larger local coil arrays on their bodies unpleasant (e.g., patients with claustrophobic tendencies, who feel uncomfortable inside the measuring chamber anyway).

The architecture of a remote body array (RBA) is one way of achieving a magnetic resonance device with a minimum number of local coils.

An antenna arrangement such as an RBA, like an array of local coils, consists of a plurality of individual antenna elements that are not positioned on the examination object or body of the patient but at a distance therefrom. The antenna elements may be located close to walls of the measuring chamber and/or on the outside of the wall of the measuring chamber, as close as possible to the high-frequency screen, in order to keep as much free space available as possible in the measuring chamber. One example of an RBA is described in WO 2007/104607 A1. To save space, the individual conductor loops of the RBA are disposed between the conductor rods of a birdcage antenna used for transmitting. With this arrangement, as with a local coil array, the antenna conductor loops used for receiving are disposed so that a conductor loop surface runs parallel to the high-frequency shield and is therefore also essentially parallel to the body surface of the examination object.

One secondary effect of such an arrangement is that eddy currents induced in the high-frequency shield may cause the magnetic field located orthogonally to the surface of the high-frequency shield to be canceled in proximity to the high-frequency shield and unwanted interference signals to be induced in the receive coils. This reduces the signal-to-noise ratio within an RBA considerably. In order to be able to achieve an adequate air gap between the RBA and the high-frequency shield, either the diameter of the RBA is reduced, with the disadvantage of reducing the diameter of the measuring chamber, or the gradient coil arrangement is enlarged in order to be able to make the high-frequency shield bigger (e.g., also with respect to diameter). If the gradient coil arrangement is enlarged, the linearity and efficiency of the gradient coil arrangement are reduced and the gradient coil arrangement consumes more power.

SUMMARY AND DESCRIPTION

The present embodiments may obviate one or more of the drawbacks or limitations in the related art. For example, a magnetic resonance device with an improved antenna arrangement may be provided.

In one embodiment of a magnetic resonance device, an antenna arrangement includes a plurality of antenna elements disposed around a measuring chamber. Each antenna element of the plurality of antenna elements includes at least one component that is active in the manner of an antenna and extends, for example, radially or obliquely radially as viewed from a high-frequency shield, towards an interior of the measuring chamber.

In other words, the components that are active in the manner of an antenna each extend, for example, in the case of a cylindrical measuring chamber, radially or obliquely radially towards a central longitudinal axis (e.g., the z-axis referred to above) of the measuring chamber. The present embodiments are not restricted to magnetic resonance devices having a measuring chamber with a cylindrical cross section but may also be used on other devices (e.g., devices with a C-shaped or portal structure having a measuring chamber that is open on one side). A component that is active in the manner of an antenna may be a part of an antenna element that has the function of the antenna per se (e.g., of receiving or transmitting), in contrast to a part that is not active in the manner of an antenna (e.g., a holder) made, for example, of non-conducting components such as plastic, which does not contribute per se to receiving or transmitting.

The present embodiments therefore provide that at least some of the antenna elements have a directional component orthogonal to the surface of the high-frequency shield in each instance. This provides that the individual antenna elements may receive an incoming magnetic resonance signal much more efficiently than is the case with antenna conductor loops in conventional RBAs. A vector of an expected magnetic field distribution outside an examination object is influenced by the external conductors (e.g., by the antenna elements of a body coil and by a surface of the high-frequency shield), since in close proximity to electrical conductors, the magnetic high-frequency fields have no components orthogonal to the surface of the relevant conductor, only components that are tangential or parallel to the surface. This is because eddy currents induced in the conductor generate counter magnetic fields that cancel the magnetic component of the incoming magnetic high-frequency field orthogonal to the conducting surface. The structure of the antenna elements with a component that is active in the manner of an antenna and extends as viewed from the high-frequency shield towards the interior of the measuring chamber provides that, unlike with a conventional RBA, the components of the magnetic high-frequency field of the magnetic resonance signal to be received running parallel or tangentially to the surface of the high-frequency shield are captured. An angle between the component that is active in the manner of an antenna and the surface of the high-frequency shield may be 15° to 90 (e.g., 30° to 90° or 45° to 90°). The antenna elements of the present embodiments are therefore better matched to the direction of the high-frequency magnetic field vector of the magnetic resonance signal and may therefore capture the magnetic resonance signal without major losses.

Embodiments of the antenna arrangement, as described above, are useful, for example, for receiving magnetic resonance signals, since the antenna arrangement is able to receive even relatively weak magnetic resonance signals with a good signal-to-noise ratio. Therefore, the antenna arrangement may also be configured accordingly as a receive antenna arrangement. In other words, electrical components and conductor tracks are designed for low outputs, so that the smallest possible signals may be received. The antenna arrangement may also include suitable preamplifier components that are connected to the antenna elements to preamplify the signals received by the antenna elements. The antenna arrangement may also be used as a transmit antenna arrangement.

In order to match the antenna elements in the best possible manner to the magnetic field direction of the magnetic resonance signals, the antenna elements may have at least one component that is active in the manner of an antenna and extends directly or at a short distance (e.g., a few mm with a maximum of 30 mm) from a surface of the high-frequency shield towards an interior of the measuring chamber.

In one embodiment, the antenna elements include antenna conductor loops, each of which is configured and disposed so that the conductor loop plane (e.g., the plane of the surface delimited by the conductor loop and therefore active in the manner of an antenna) is disposed at least in parts orthogonally or obliquely orthogonally to the surface of the high-frequency shield. The conductor loop plane has a vector component that runs radially inwards from the high-frequency shield. This provides that the vector components of the high-frequency magnetic field of the magnetic resonance signal running tangentially or parallel to the high-frequency shield are captured efficiently by the conductor loop, and a corresponding signal is induced in the conductor loop.

The antenna arrangement may, as with a conventional RBA, include an antenna array having a plurality of individually operable antenna conductor loops. The antenna conductor loops may have a width between 10 cm and 50 cm (e.g., between 20 cm and 35 cm). This may be the width of an area spanned by the antenna conductor loop. The antenna conductor loops may also have such measurements in length.

The antenna conductor loops may have any shape. However, on a side of the high-frequency shield facing the measuring chamber of the magnetic resonance device, the antenna conductor loops may have a segment that runs parallel to and at a distance from a surface of the high-frequency shield. In other words, this segment runs at a defined distance parallel to the surface of the high-frequency shield.

The antenna conductor loops may also include a conductor loop part in the form of a segment of the high-frequency shield. In other words, the high-frequency shield also forms part of the antenna.

In one embodiment, the antenna conductor loops each run through guides in the high-frequency shield from a side facing the measuring chamber of the magnetic resonance device to a rear of the high-frequency shield. There, the antenna conductor loops may be connected to a signal processing unit, for example, first to a preamplifier or the like.

In order to achieve inductive decoupling of adjacent antenna conductor loops, two adjacent antenna conductor loops may each be configured and disposed so that the two adjacent antenna conductor loops partially overlap. In one embodiment, the adjacent antenna conductor loops may have an overlapping region on a side of the high-frequency shield facing away from the measuring chamber of the magnetic resonance device. In this embodiment, the antenna conductor loops are passed through guides in the high-frequency shield from the side facing the measuring chamber of the magnetic resonance device to a rear such that the overlapping region is produced between adjacent antenna conductor loops, thereby achieving inductive decoupling.

At least two antenna conductor loops of an antenna array may be disposed so that conductor loop planes of the at least two antenna conductor loops running orthogonally or obliquely orthogonally to the surface of the high-frequency shield run at right angles to one another (e.g., perpendicular to one another). In one embodiment, the antenna conductor loops of an antenna array are disposed so that the conductor loop planes running orthogonally or obliquely orthogonally to the surface of the high-frequency shield run alternately parallel to the longitudinal axis of the magnetic resonance device or perpendicular to the longitudinal axis of the magnetic resonance device.

Two antenna conductor loops, the conductor loop planes of which run at right angles to one other, may cross on the side of the high-frequency shield facing the measuring chamber. In this embodiment, for example, at least one antenna conductor loop running parallel to the longitudinal axis of the magnetic resonance devices and one adjacent antenna conductor loop running perpendicular to the longitudinal axis of the magnetic resonance device may always cross.

In one embodiment, the conductor loop planes of at least two adjacent conductor loops are tilted towards one another in a V-shape in relation to a (virtual) plane of symmetry perpendicular to a surface of the high-frequency shield. This provides that the two adjacent conductor loops are tilted away from one another in relation to the plane of symmetry, with a (virtual) vertical line of the V-shape lying in the plane of symmetry. This embodiment is, for example, advantageous when magnetic resonance signals are to be received from an active layer in which the plane of symmetry lies. The pair of antenna conductor loops tilted towards the excited layer allows the maximum magnetic flux of the magnetic resonance signal to be received. If the signals are received in a parallel manner from the two antenna elements tilted towards one another, the signal-to-noise ratio is higher than that of an individual antenna conductor loop. Alternatively, the coils may also be used to perform parallel imaging and thus to reduce measuring time.

Alternatively or in addition to the antenna conductor loops, the antenna arrangement may also include antenna elements in the form of dipole elements that run orthogonally or obliquely orthogonally to the surface of the high-frequency shield inwards to the measuring chamber. For example, in ultra-high-field tomography systems (e.g., magnetic resonance tomography systems with a very high basic magnetic field of 3 Tesla or more), the electromagnetic radiation in proximity to the high-frequency shield also has a significant oscillating electrical component that is essentially orthogonal to the conducting surface of the high-frequency shield. According to the one embodiment, the orientation of the electric dipoles is therefore also optimized so that a sensitivity profile of the electric dipole is matched to the local orientation of the electric field lines to be measured. By using electric dipoles (e.g., in combination with the antenna conductor loops described above), it is possible to achieve even stronger receive signals in the antennas.

It is also advantageously possible with the structure for at least some of the antenna elements to be disposed between rods of a standard birdcage antenna.

The antenna arrangement may be configured so that the antenna arrangement encloses the measuring chamber completely. Since the problem of the biggest possible free space relates, for example, to a region of the measuring chamber above the patient table, it is adequate if, according to one embodiment, only an upper region of the measuring chamber is provided with one embodiment of an antenna arrangement close to the high-frequency shield. In a lower region, conventional coil arrays integrated in the patient table (e.g., spine coils) may be used. The coils may also be supported in a movable or displaceable manner within the table, so that the coils remain in the same z-position in a field of view when the patient table is moved in the z-direction (e.g., to reposition the examination object within the field of view).

The antenna elements may be made from any conducting material (e.g., copper or the like). The conductor loops may be produced in a simple variant in the form of copper wires or printed copper tracks on a flexible board material.

In one embodiment, the antenna elements (e.g., the antenna conductor loops) are formed from carbon nano tube (CNT) wires. The CNT wires are characterized by small losses and little noise at high frequencies. The CNT filaments may be oriented essentially in a direction of the expected current flow. Similarly, the antenna elements may be formed by high-temperature superconductors (HTS materials) and may be additionally cooled to reduce noise.

DETAILED DESCRIPTION OF THE DRAWINGS

Figure 1:
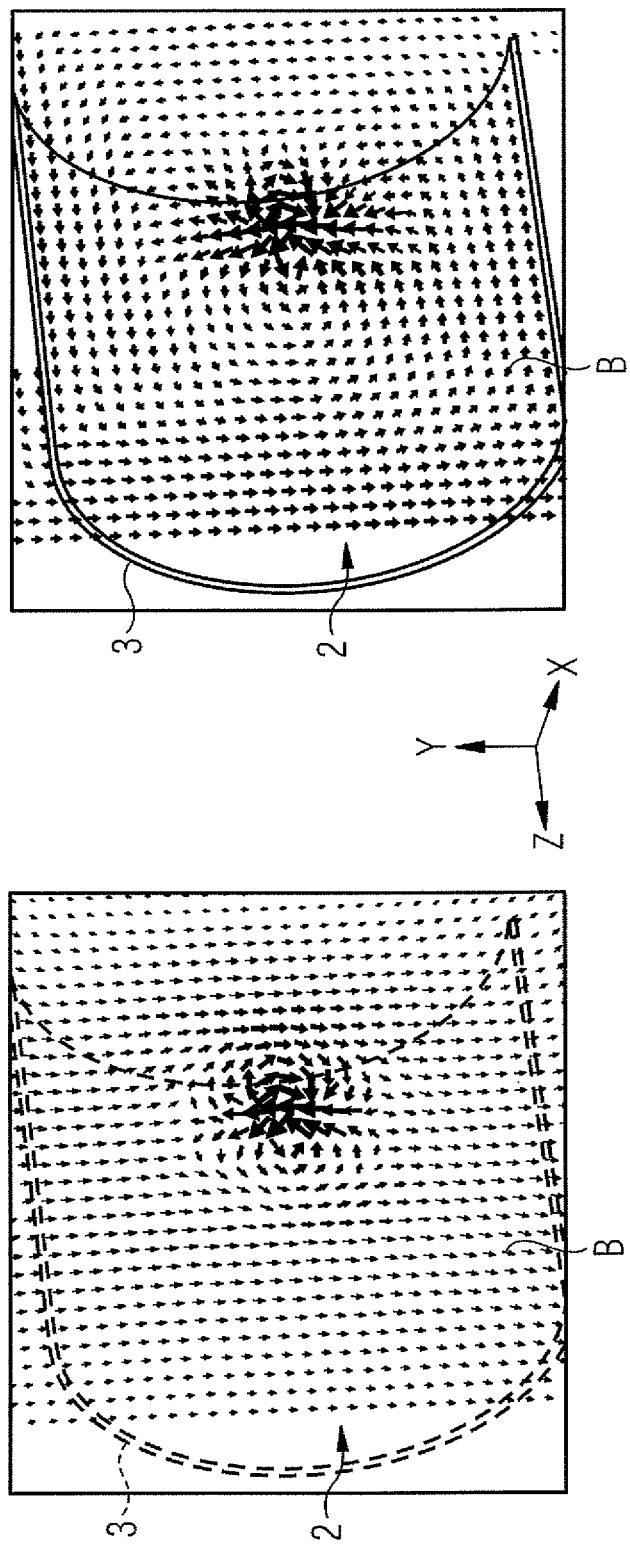
FIG. 1 shows a diagram of a simulated high-frequency magnetic field distribution of a magnetic resonance signal for comparison with a configuration without a high-frequency shield (left side) and a configuration with a high-frequency shield (right side)

FIG. 1 shows the result of simulations of a high-frequency magnetic field distribution B that occurs when a simple magnetic high-frequency dipole generates an oscillating field with a frequency of 300 MHz in a 7 Tesla magnetic field in a measuring chamber 2 of a magnetic resonance device. This corresponds to the transmitted magnetic resonance signal of a water proton in a 7 Tesla magnetic field. The diagrams in FIG. 1 each show one layer of the magnetic field distribution within a layer running parallel to the z-axis of the magnetic resonance device. Disposed on the right is a half shell of a high-frequency shield 3 disposed in a circular manner around the measuring chamber 2 (e.g., represented in FIG. 1 by a simple semi-cylindrical conductor surface). Shown on the left side with a broken line is the position of the high-frequency shield for comparison purposes. Of interest in these simulations is the behavior of the magnetic field lines in the region of the high-frequency shield. While in the simulation shown on the left without a high-frequency shield, the magnetic field lines also run radially outwards in the outer region, in the simulation shown on the right, the magnetic field lines in proximity to the high-frequency shield 3 are influenced by the high-frequency shield 3 so that the magnetic field lines run parallel or tangentially to the high-frequency shield 3.

Since magnetic field components of the transmitted magnetic resonance signal are to be received by antennas, the idea behind the present embodiments is not to structure antenna elements as antenna conductor loops running parallel or tangentially to the high-frequency shield 3 but to structure the antenna elements so that the antenna elements project at least partially perpendicular to a surface of the high-frequency shield 3 into the measuring chamber 2. This provides that the antenna elements are better matched to the high-frequency magnetic field lines to be captured locally.

Figure 2:
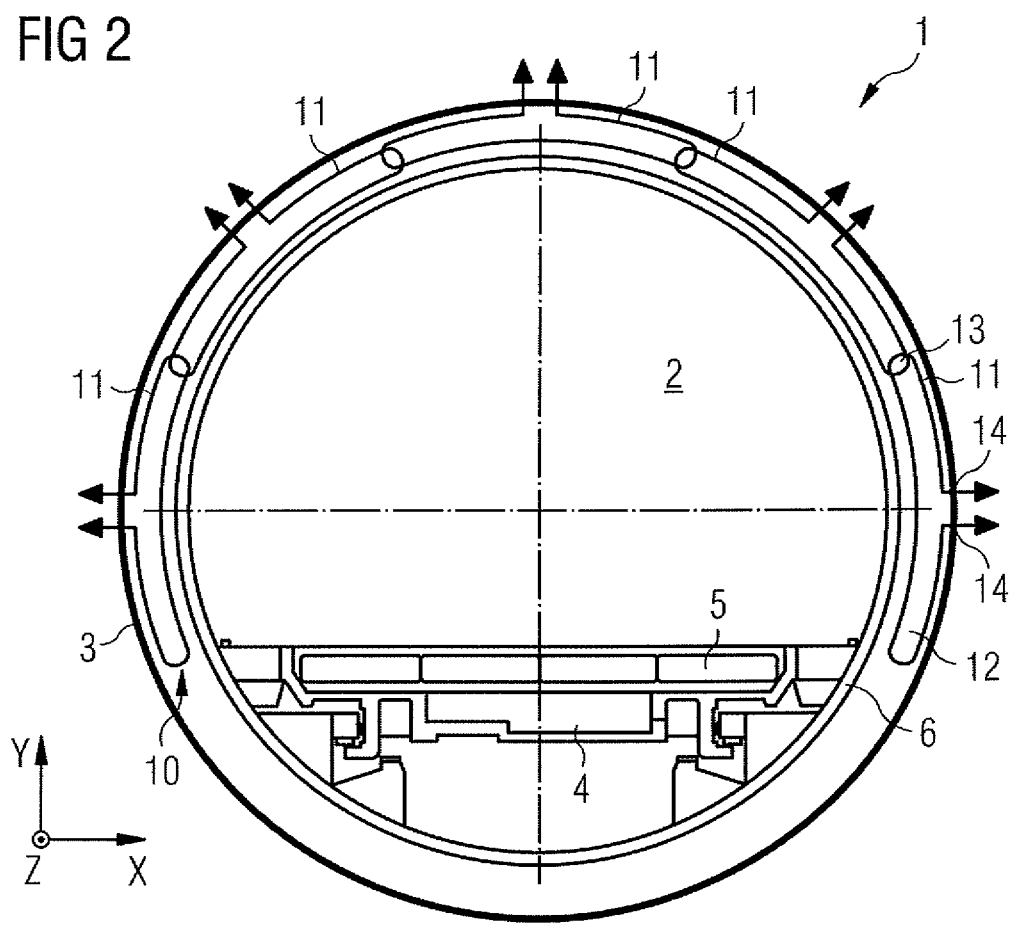
FIG. 2 shows a cross section through a magnetic resonance device having one embodiment of an antenna arrangement.

FIG. 2 shows components around the measuring chamber 2 of the magnetic resonance device 1 having one embodiment of an antenna arrangement 10.

The measuring chamber 2 shown in FIG. 2 is delimited by a cylindrical tube 6 made of a suitable plastic. A patient table 4 is disposed in a lower region of the measuring chamber 2 within the cylindrical tube 6, such that the patient table 4 may be displaced in the z-direction. A high-frequency shield 6 is disposed outside and around the cylindrical tube 6 at a radial distance from the cylindrical tube 6 is a high-frequency shield 3. The high-frequency shield 3 may be attached to the inside of a gradient coil system (not shown) similarly disposed around the measuring chamber 2.

The magnetic resonance device may include a standard body coil (also not shown in FIG. 2 for greater clarity) such as, for example, a birdcage antenna. The birdcage antenna may be attached, for example, in the form of conductor tracks to a further tube that is disposed between the cylindrical tube 6 and the high-frequency shield 3. The body coil may be used, for example, to transmit the high-frequency signals for MR excitation. Alternatively or additionally, one embodiment of the antenna arrangement 10 may also be structured so that the antenna arrangement may be used in both transmit mode and in receive mode.

One embodiment of the permanently installed antenna arrangement 10 includes a plurality of antenna conductor loops 11 in a region above the patient table 4. Each of the plurality of antenna conductor loops 11 is shaped so that conductor loop planes of the plurality of antenna conductor loops 11 extend from the high-frequency shield 3 inwards between the high-frequency shield 3 and the cylindrical tube 6.

The antenna conductor loops 11 are passed outwards to guides through the high-frequency shield 3 and are connected on the outside, for example, to preamplifiers (not shown) that may forward the preamplified signal to a conventional receive facility (e.g., a receiver) of the magnetic resonance device.

In embodiment shown in FIG. 2, the antenna conductor loops 11 are configured so that the antenna conductor loops 11 each enclose a region in the shape of a ring segment within the space between high-frequency shield 3 and cylindrical tube 6. The ring segment runs parallel to the surface of the cylindrical tube 6 or an inner surface of the high-frequency shield 3. A conductor loop plane 12 spanned by the ring segment is perpendicular to the surface of the cylindrical tube 6 and the surface of the high-frequency shield 3. Adjacent antenna elements 11 overlap at ends in an overlap region 13. This provides that the adjacent antenna elements 11 are decoupled inductively from one another.

FIG. 2 shows a cross section at a z-position through the magnetic resonance device 1, so that only a partial antenna arrangement with a row of antenna conductor loops 11 is visible. With this structure, there may be a plurality of partial antenna arrangements in planes lying one behind the other in the z-direction, so that the entire antenna arrangement 10 includes an array of antenna elements 11 disposed in two directions (e.g., one circular direction parallel to the high-frequency screen 2 and one parallel to the z-direction).

In the lower region of the measuring chamber 2, below the patient table 4, the antenna conductor loops 11 are not required, since a conventional antenna array 5 (e.g., a spine array) is disposed in the patient table 4 instead. The spine array 5 may be disposed in the patient table 4 so that the spine array 5 may be moved independently and may also remain in a fixed z-position relative to the antenna arrangement 10, for example, when the patient table 4 is moved.

A comparison of one embodiment of the antenna array 10 with the simulation of the field line profile of the high-frequency magnetic field B of a high-frequency signal transmitted in the measuring chamber 2 (e.g., as shown on the right in FIG. 1) shows that the antenna conductor loops 11 of the antenna array 10 are suited to capturing the magnetic field lines close to the high-frequency shield 3, with a particularly good receive signal being induced in the antenna conductor loops 11 as a result.

Figure 3:
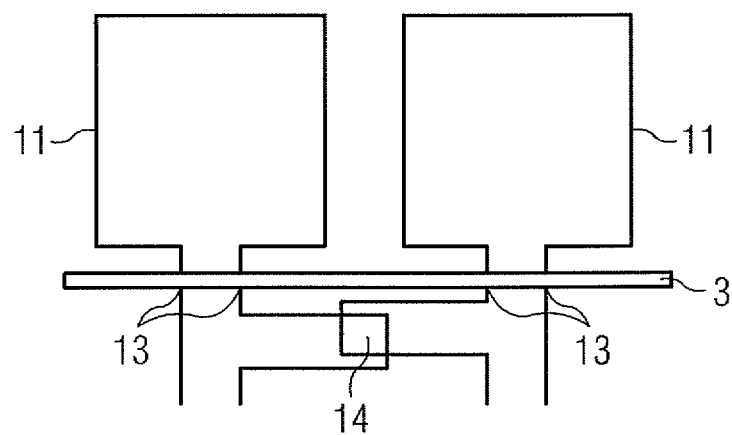
FIG. 3 shows a schematic diagram of a possible inductive decoupling of one embodiment of two adjacent antenna conductor loops.

FIG. 3 shows one embodiment used to decouple adjacent antenna conductor loops 11 inductively from one another. The antenna conductor loops 11 on a side of the high-frequency shield 3 facing the measuring chamber 2 show no overlap. Instead, however, on the outside of the high-frequency shield 3 before the antenna conductor loops 11 are fed to the preamplifier (not shown), the conductor tracks are shaped so that an overlap region 14 is produced, resulting in inductive decoupling.

FIGS. 4 to 8 show example embodiments of the antenna arrangements.

Figure 4:
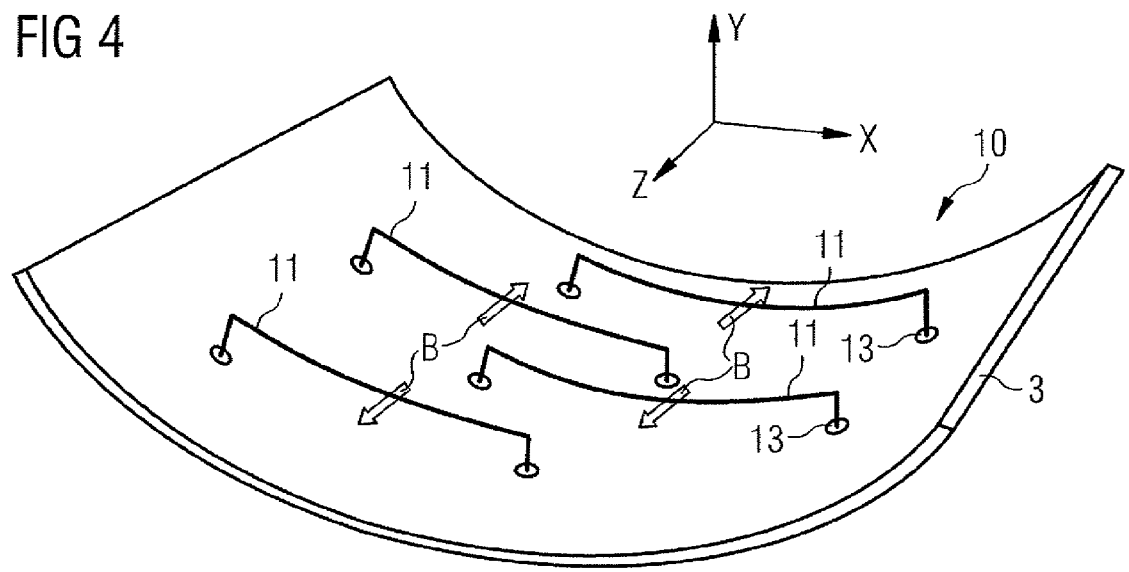
FIG. 4 shows a perspective top view of a part of one embodiment of a magnetic resonance antenna arrangement.

FIG. 4 shows a section of a high-frequency shield 3, in which the antenna conductor loops 11, in contrast to FIG. 2, are again fed closer to one another, not on the inside (e.g., the side of the high-frequency shield 3 facing the measuring chamber), with the result that a complete conductor loop is configured by a conductor wire or the like in the measuring chamber 2 in front of the high-frequency shield 3. Instead, only a segment of each of the conductor loops 11 runs tangentially on the inside of the high-frequency shield 3 parallel to a surface of the conductor loop 1, and at the ends, the antenna conductor loops 11 are passed respectively through guides 13 to a rear of the high-frequency shield 3. On the rear, the ends of the conductor loops 11 are connected, for example, to a high-frequency preamplifier. In this embodiment, the effective conductor loop is therefore also formed in part by the high-frequency shield 3. In other words, a part of the high-frequency shield 3 (e.g., the surface segment below the parallel segment of the antenna conductor loop 11) in each instance forms a part of the antenna element 11. The antenna array 10 is thus virtually integrated in the high-frequency shield 3. This has the advantage that field lines may also be captured directly in front of the surface of the high-frequency shield 3, and the space is utilized particularly efficiently.

Figure 5:
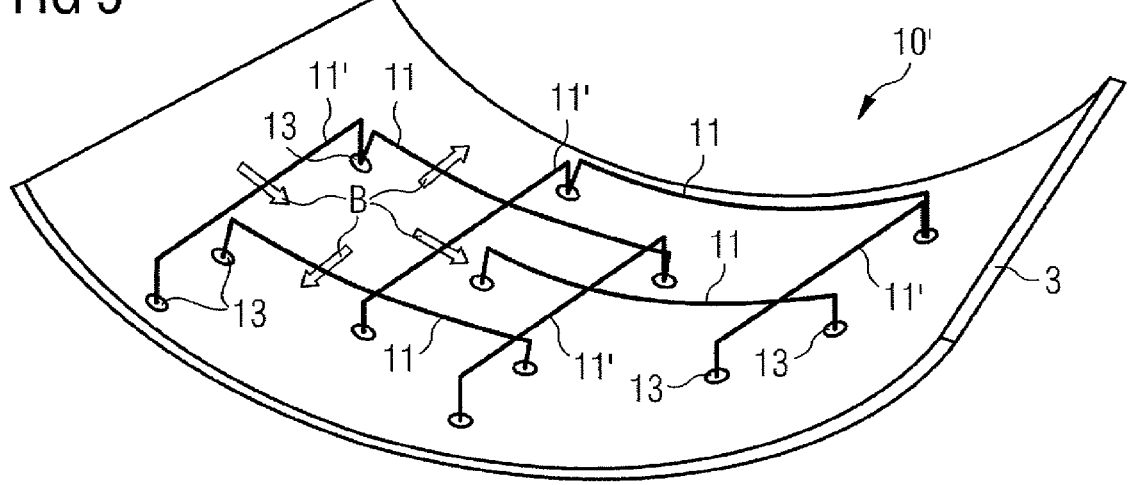
FIG. 5 shows a perspective top view of a part of one embodiment of a magnetic resonance antenna arrangement.

FIG. 5 shows a variant of the embodiment shown in FIG. 4. In this antenna arrangement 10', as in the exemplary embodiments according to FIGS. 2 and 4, a plurality of antenna conductor loops 11 is disposed tangentially to the surface of the high-frequency shield 3, while other antenna conductor loops 11' run parallel to the z-axis of the magnetic resonance device. In this embodiment, the magnetic field components running tangentially to the surface of the high-frequency shield 3 are also captured particularly efficiently. The arrangement is configured such that some of the antenna conductor loops 11, 11' cross to produce inductive decoupling between the antenna conductor loops 11, 11'.

Figure 6:
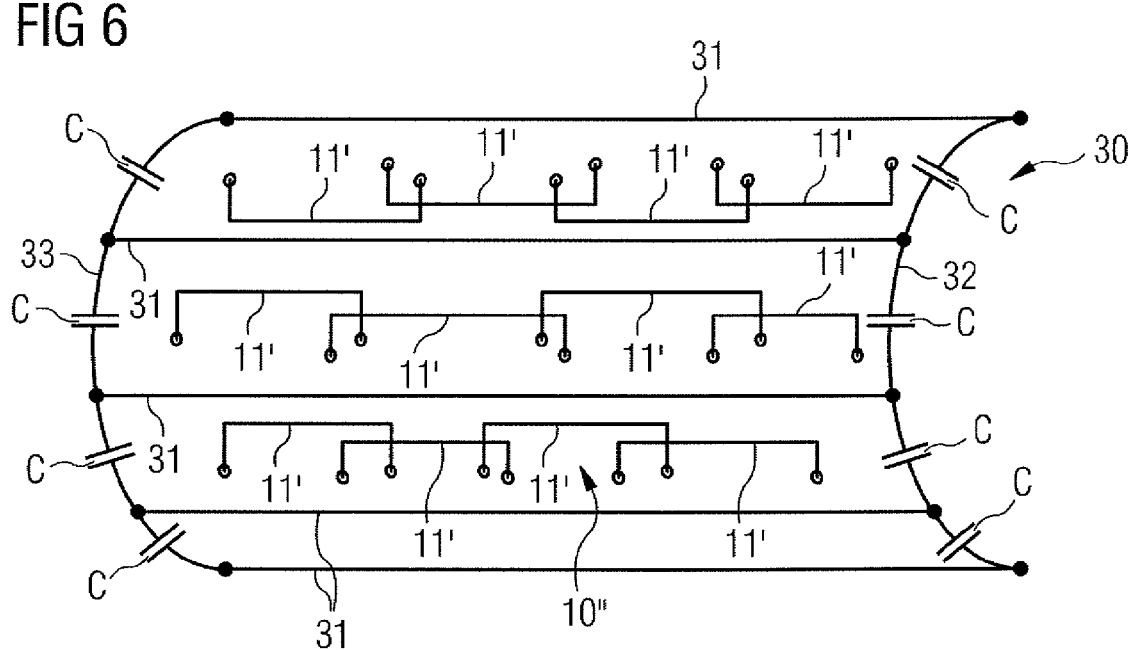
FIG. 6 shows a part of one embodiment of an antenna arrangement.
Figure 7:
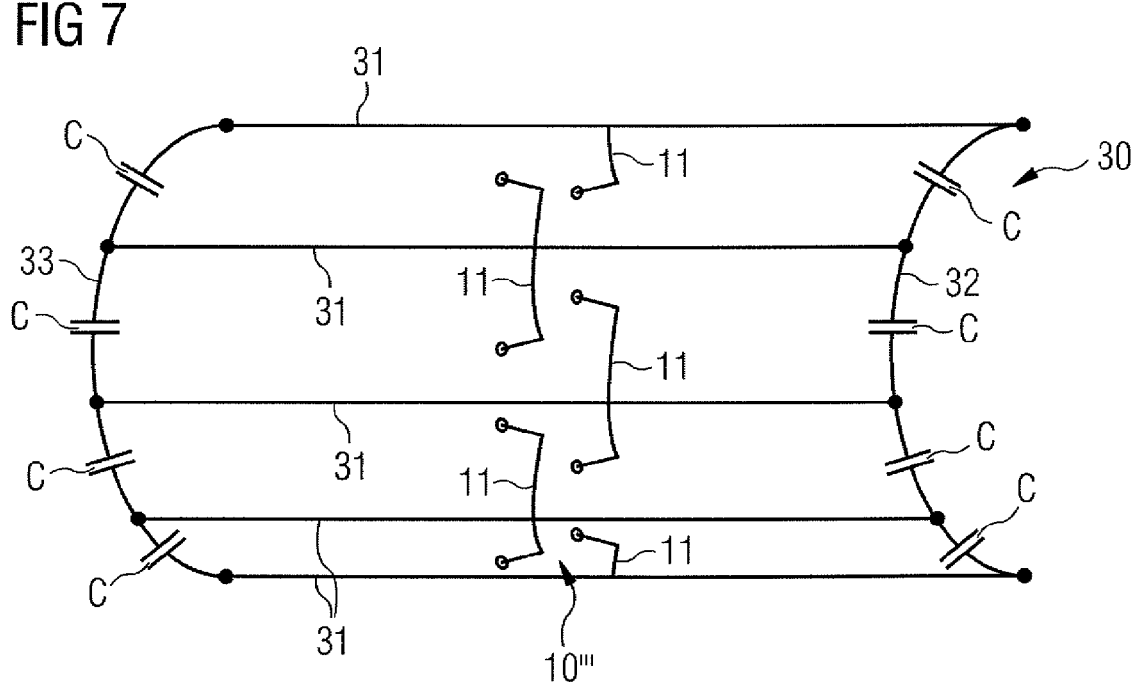
FIG. 7 shows a part of one embodiment of an antenna arrangement.

FIGS. 6 and 7 show two respective exemplary embodiments of how an antenna arrangement 10", 10'" may also be disposed between rods of a birdcage antenna 30. This birdcage antenna 30 consists of longitudinal antenna rods 31 that are each connected to one another at an end by end rings 32, 33. Between connection points of the transmit rods to the end rings 32, 33, the end rings are interrupted by capacitors C that respectively form reactances of the birdcage antenna 30.

In the exemplary embodiment according to FIG. 6, one embodiment of the antenna arrangement 10" is configured so that each of the antenna conductor loops 11' run parallel to the z-axis and therefore also parallel to the longitudinal rods 31 of the birdcage antenna 30. A row of antenna elements 11' is disposed, in each instance, within a segment formed by two longitudinal rods 31 of the birdcage antenna 30, so that the antenna elements 11' overlap in an end region to achieve inductive decoupling from one another.

In the variant according to FIG. 7, the antenna elements 11 are disposed tangentially to the surface of the high-frequency shield 3 and therefore run parallel to the end rings 32, 33 of the birdcage antenna 30. The antenna arrangement 10''' shown in FIG. 7 corresponds essentially to an arrangement also shown in FIG. 4. Each of the conductor loops 11 is configured so that the conductor loop 11 bridges a longitudinal rod 31 of the birdcage antenna 30. In the exemplary embodiment according to FIG. 7, a plurality of rows of antenna elements 11 disposed in a ring may be disposed next to one another in the z-direction.

One embodiment of an antenna arrangement may also be configured as a combination of the antenna arrangement 10" according to FIG. 6 and the antenna arrangement 10''' according to FIG. 7, producing a similar result to the antenna arrangement in FIG. 5.

Figure 8:
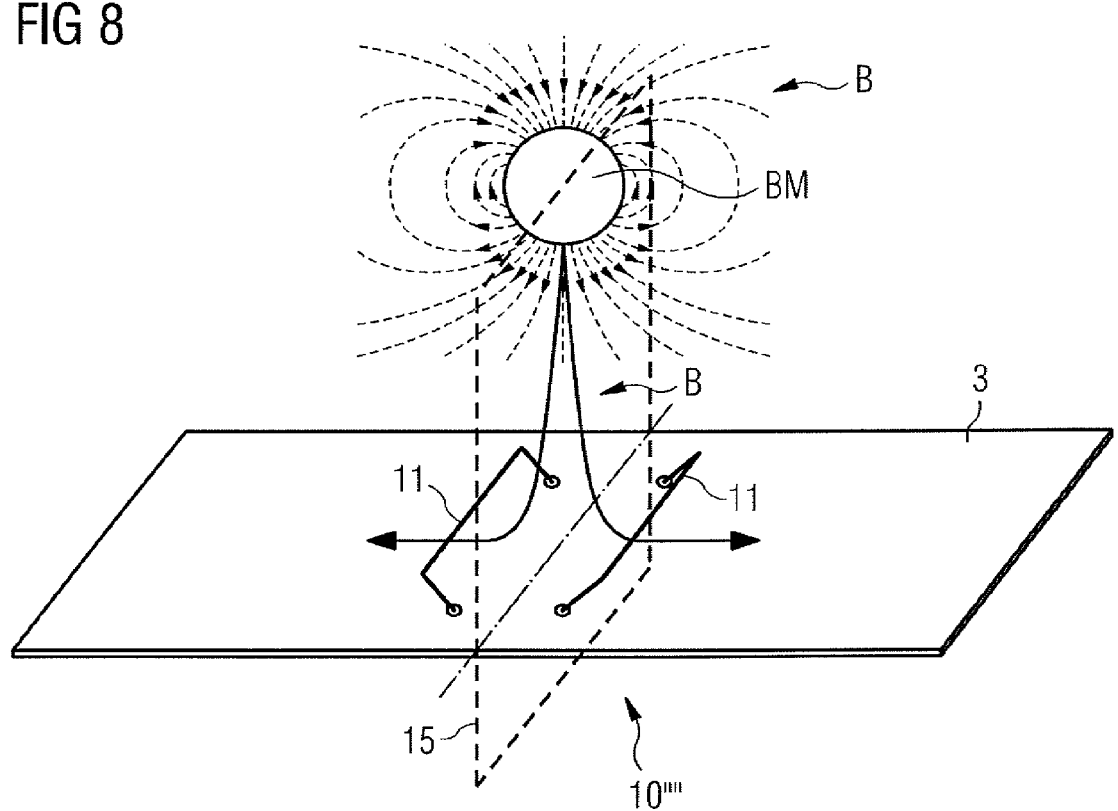
FIG. 8 shows a part of one embodiment of an antenna arrangement.

FIG. 8 shows a further exemplary embodiment having antenna conductor loops 11, only some of which are on the inside of the high-frequency shield 3 and therefore respectively form an effective antenna conductor loop together with the high-frequency shield 3. In the antenna arrangement 10'''', however, the antenna conductor loops 11 are tilted towards one another in a V-shape in relation to a virtual plane of symmetry 15. The plane of symmetry 15, for example, is located in a center of a spherical homogeneity volume BM of the static magnetic field of the magnetic resonance devices represented as a simple sphere. The two antenna conductor loops 11 are positioned so that in the z-direction (e.g., perpendicular to the plane of symmetry 15), the two conductor loops 11 lie in front of or behind a homogeneity volume BM. If the two antenna conductor loops 11 that are tilted towards one another are operated in a parallel manner, the two conductor loops 11 each receive deflected magnetic field lines of a magnetic resonance signal that is transmitted in a region of the homogeneity volume BM of the magnetic resonance device particularly efficiently on both sides of the surface of the high-frequency shield 3 and thus measure the deflected magnetic field lines with a particularly good signal to noise ratio. Alternatively, the two antenna conductor loops 11 may also be operated individually and be used, for example, like the individual antenna conductor loops in the exemplary embodiments described above to perform parallel imaging and thus to shorten the measuring time.

In the case of ultra-high magnetic field strengths, for example, it may also be expected that the electromagnetic field in proximity to the high-frequency shield 3 is propagated along the high-frequency shield and separates, for example, in the z-direction. It is therefore possible with the antenna arrangement 10'''' according to FIG. 8 for the magnetic resonance signal still to be measured very efficiently even more remotely from the active layer, from which the magnetic resonance signals are sent.

As shown in FIG. 7, also in the exemplary embodiment according to FIG. 8, a number of pairs of conductor loops 11 tilted in a V-shape towards one another may also be disposed in a parallel manner along the plane of symmetry 15 in a ring shape around the entire measuring chamber 2 or at least an upper part of the measuring chamber 2. It is also possible for a number of coils to be disposed next to one another in different planes parallel to the plane of symmetry 15.

Figure 9:
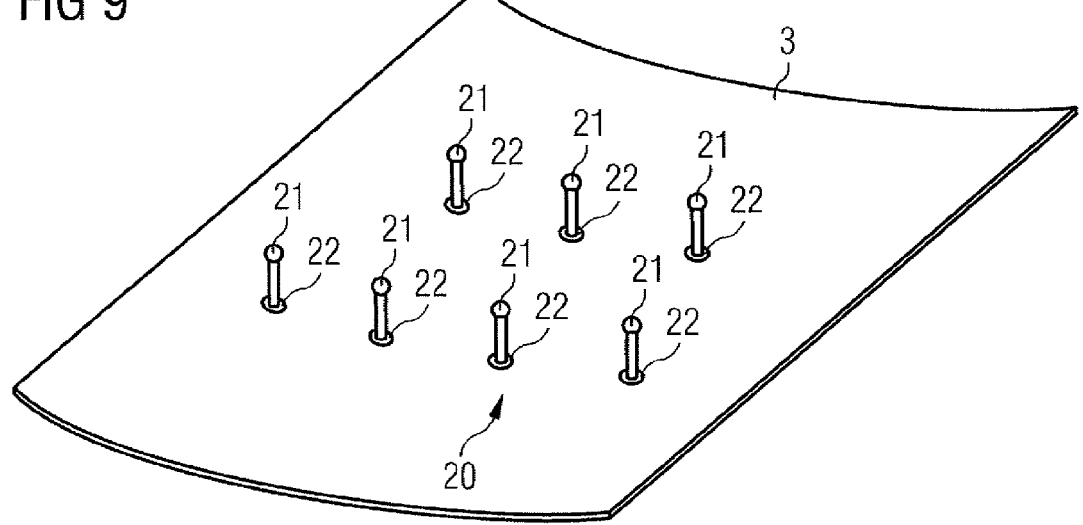
FIG. 9 shows a part of one embodiment of an antenna arrangement.

FIG. 9 shows a further exemplary embodiment of antenna elements 21 of an antenna arrangement 20. The antenna elements 21 are configured as pure dipole antenna rods 21 that project from the inner surface of the high-frequency shield 3 into the measuring chamber 2 through guides 22. The dipole antenna rods 21 may receive an E-field component of the magnetic resonance signal. In ultra-high-field applications, for example, the electromagnetic radiation of the magnetic resonance signal in proximity to the high-frequency shield 3 also has a significant oscillating electrical component that is disposed orthogonally to the conducting surface of the high-frequency shield 3 and may therefore be captured efficiently with said antenna elements 21.

In one embodiment, the antenna arrangement may also include both variants of antenna elements (e.g., both antenna conductor loops 11, 11'), which primarily capture the magnetic field component of the magnetic resonance signal, and dipole antenna elements 21, as shown in FIG. 9, to detect the alternating electric field of the high-frequency signal. Suitable combinations therefore allow good receive signals to be achieved.

The structures illustrated specifically in the figures are exemplary embodiments, and the basic principle of the embodied antenna arrangement may also be varied without departing from the scope of the invention, as defined by the claims. For example, CNT wires or wires made of high-temperature superconductor material may be used instead of the simple conductor wires illustrated in the figures. The use of the indefinite article "a" does not preclude the possibility of the relevant features also being present in greater numbers.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A magnetic resonance device comprising:
a measuring chamber;
a high-frequency shield at least partially enclosing the measuring chamber; and
an antenna arrangement comprising:
a plurality of antenna elements disposed around the measuring chamber; and
at least one component that is active as an antenna and extends towards an interior of the measuring chamber as viewed from the high-frequency shield.

2. The magnetic resonance device as claimed in claim 1, wherein the plurality of antenna elements includes the at least one component that is active as the antenna and extends directly or at a short distance from a surface of the high-frequency shield towards the interior of the measuring chamber.

3. The magnetic resonance device as claimed in claim 2, wherein the antenna arrangement is configured as a receive antenna arrangement.

4. The magnetic resonance device as claimed in claim 1, wherein the antenna arrangement is configured as a receive antenna arrangement.

5. The magnetic resonance device as claimed in claim 4, wherein the plurality of antenna elements comprises antenna conductor loops, each of the conductor loops being configured so that a conductor loop plane is disposed, at least in parts, orthogonally or obliquely orthogonally to a surface of the high-frequency shield.

6. The magnetic resonance device as claimed in claim 1, wherein the plurality of antenna elements comprises antenna conductor loops, each of the conductor loops being configured so that a conductor loop plane is disposed, at least in parts, orthogonally or obliquely orthogonally to a surface of the high-frequency shield.

7. The magnetic resonance device as claimed in claim 6, wherein the antenna arrangement comprises an antenna array having a plurality of antenna conductor loops, the plurality of antenna elements comprising the plurality of antenna conductor loops.

8. The magnetic resonance device as claimed in claim 7, wherein at least two antenna conductor loops of the antenna array are disposed so that conductor loop planes of the at least two antenna conductor loops running orthogonally or obliquely orthogonally to the surface of the high-frequency shield, run at right angles to one another.

9. The magnetic resonance device as claimed in claim 8, wherein the at least two antenna conductor loops, the conductor loop planes of which run at right angles to one another, cross on a side of the high-frequency shield facing the measuring chamber.

10. The magnetic resonance device as claimed in claim 7, wherein each antenna conductor loops of the plurality of antenna conductor loops includes a segment on a side of the high-frequency shield facing the measuring chamber, the segment running parallel to and at a distance from the surface of the high-frequency shield.

11. The magnetic resonance device as claimed in claim 7, wherein two adjacent antenna conductor loops of the plurality of antenna conductor loops are configured and disposed so that the two adjacent antenna conductor loops partially overlap to achieve inductive decoupling of the adjacent antenna conductor loops.

12. The magnetic resonance device as claimed in claim 6, wherein each of the antenna conductor loops includes a segment on a side of the high-frequency shield facing the measuring chamber, the segment running parallel to and at a distance from the surface of the high-frequency shield.

13. The magnetic resonance device as claimed in claim 12, wherein the antenna conductor loops comprise a conductor loop part in the form of a segment of the high-frequency shield.

14. The magnetic resonance device as claimed in claim 6, wherein the antenna conductor loops comprise a conductor loop part in the form of a segment of the high-frequency shield.

15. The magnetic resonance device as claimed in claim 6, wherein the antenna conductor loops run through guides in the high-frequency shield from a side facing the measuring chamber to a rear of the high-frequency shield.

16. The magnetic resonance device as claimed in claim 6, wherein two adjacent antenna conductor loops are configured and disposed so that the two adjacent antenna conductor loops partially overlap to achieve inductive decoupling of the adjacent antenna conductor loops.

17. The magnetic resonance device as claimed in claim 16, wherein the two adjacent antenna conductor loops include an overlapping region on a side of the high-frequency shield facing away from the measuring chamber.

18. The magnetic resonance device as claimed in claim 6, wherein conductor loop planes of at least two adjacent conductor loops are tilted towards one another in a V-shape in relation to a plane of symmetry perpendicular to the surface of the high-frequency shield.

19. The magnetic resonance device as claimed in claim 1, wherein the plurality of antenna elements comprises dipole elements that run orthogonally or obliquely orthogonally to a surface of the high-frequency shield inwards to the measuring chamber.

20. The magnetic resonance device as claimed in claim 1, wherein at least some antenna elements of the plurality of antenna elements are disposed between longitudinal antenna rods of a birdcage antenna.

* * * * *